United States Patent [19]

Nagy et al.

[11] Patent Number: 5,328,906
[45] Date of Patent: Jul. 12, 1994

[54] 0-(3-AMINO-2-HYDROXYPROPYL)-HYDROXIMIC ACID HALIDES AND PROCESS FOR PREPARING THE SAME

[75] Inventors: Peter L. Nagy; Bela Balazs; Maria Boross; Jeno Szilbereky; Gizella Zsila; Lajos Abraham; Gyorgy Blasko; Bela Gachalyi; Attila Almasi; Gabor Nemet, all of Budapest, Hungary

[73] Assignee: Biorex Kutato-Fejleszto KFT, Budapest, Hungary

[21] Appl. No.: 72,765

[22] Filed: Jun. 7, 1993

Related U.S. Application Data

[60] Continuation-in-part of Ser. No. 906,402, Jul. 1, 1992, Pat. No. 5,296,606, which is a division of Ser. No. 499,318, Jun. 28, 1990, Pat. No. 5,147,879.

[51] Int. Cl.$^5$ .................. A61K 31/47; C07D 401/12; C07D 413/12; C07D 471/06
[52] U.S. Cl. .................. 514/235.5; 514/255; 514/307; 544/124; 544/162; 544/360; 544/398; 546/145
[58] Field of Search ............... 544/124, 162, 360, 398; 546/145; 514/235.5, 255, 307

[56] References Cited

U.S. PATENT DOCUMENTS

| | | | |
|---|---|---|---|
| 3,673,188 | 6/1972 | Harsanyi | 546/145 |
| 4,187,220 | 2/1980 | Takacs | 546/193 |
| 4,308,399 | 12/1981 | Takacs | 564/257 |
| 5,239,077 | 8/1993 | Bertok et al. | 546/193 |

FOREIGN PATENT DOCUMENTS 2738589  8/1987  Fed. Rep. of Germany.

Primary Examiner—C. Warren Ivy
Assistant Examiner—Celia Chang
Attorney, Agent, or Firm—Ladas & Parry

[57] ABSTRACT

Hydroximic acid derivatives of the formula

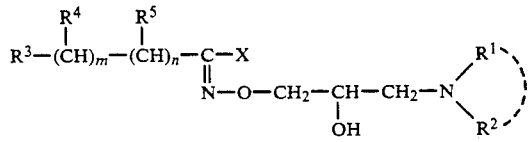

These compounds are useful for treating diabetes angiopathy.

3 Claims, 3 Drawing Sheets

O-(3-AMINO-2-HYDROXYPROPYL)-HYDROXIMIC ACID HALIDES AND PROCESS FOR PREPARING THE SAME

This is a continuation-in-part of copending application Ser. No. 07/906,402 filed on Jul. 1, 1992, now U.S. Pat. No. 5,296,606, which is a division of application Ser. No. 07/499,318 filed Jun. 28, 1990, now U.S. Pat. No. 5,147,879, and International application PCT/HU89/00048 filed on Oct. 19, 1988 and which designated the U.S.

TECHNICAL FIELD

The present invention relates to novel hydroximic acid halides, the preparation of the same, pharmaceutical compositions containing the above novel compounds as active ingredient as well as the use of the said compounds in the therapy of diabetic angiopathy.

BACKGROUND ART

One of the most frequent metabolism diseases is diabetes mellitus, the main symptom of which is the disturbance of the balance of carbohydrate metabolism in the organism. Diabetes mellitus is often accompanied by pathological vascular deformations, e.g. vasoconstrictions in the limbs, pathological deformation of the eye-ground vessels, etc. Though, in addition to insulin a number of effective drugs are known, in the field of the treatment of diabetic angiopathy associated with the basic disease, results provided by the commercially available compositions are quite poor. This situation is caused by the phenomenon that diabetes mellitus results in changes of the vascular adrenergic receptors, and consequently, medical treatment with the commercially available drugs results in adrenergic reaction different from those taking place in the blood vessels of non-diabetic patients. (Nature New Biology, 243, No. 130, 276 /1973/; Szemészet, 111, 23 /1974/; Endocrinology, 93, 752 /1973/). The adrenergic receptors of blood vessels in diabetic patients undergo a transformation into beta receptors due to the quantitative increase of the metabolism. For the receptor transformation, the release of a modulator is responsible (Amer. J. Physiol., 218, 869 /1970/). After addition of the modulator to the alpha organ the alpha agonists will not be active any more as the receptor is transformed into beta.

The original alpha sensibility may be recovered by adding a special beta blocking agent into the organism.

In case of qualitative alteration of the metabolism in model or human in vivo diabetes the alpha agonists, e.g. noradrenalin, remain effective, this effect, however, may be compensated by the addition of beta blocking agents. This is the first functional change which is detectable in diabetes, e.g. by addition of Alloxane (Hexahydropirimidin-tetraon), 24 hours after the administration. In case of diabetes an imperfect alpha-beta receptor transformation—possibly due to the formation of an alternative, so-called "Falsch" modulator—serves as starting point of the pathological changes.

DISCLOSURE OF THE INVENTION

Figure 1:
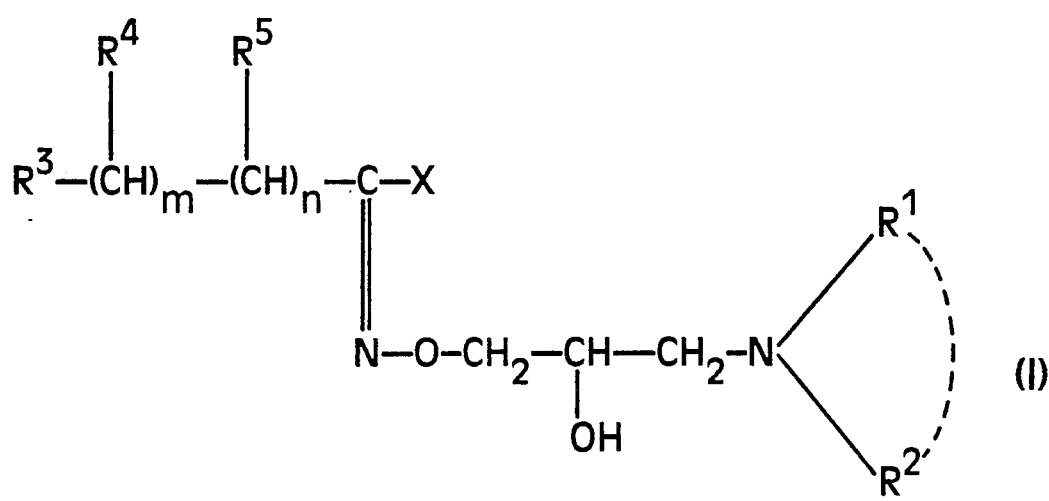
FIG. 1 is a hydroximic acid halide represented by formula (I).
Figure 2:
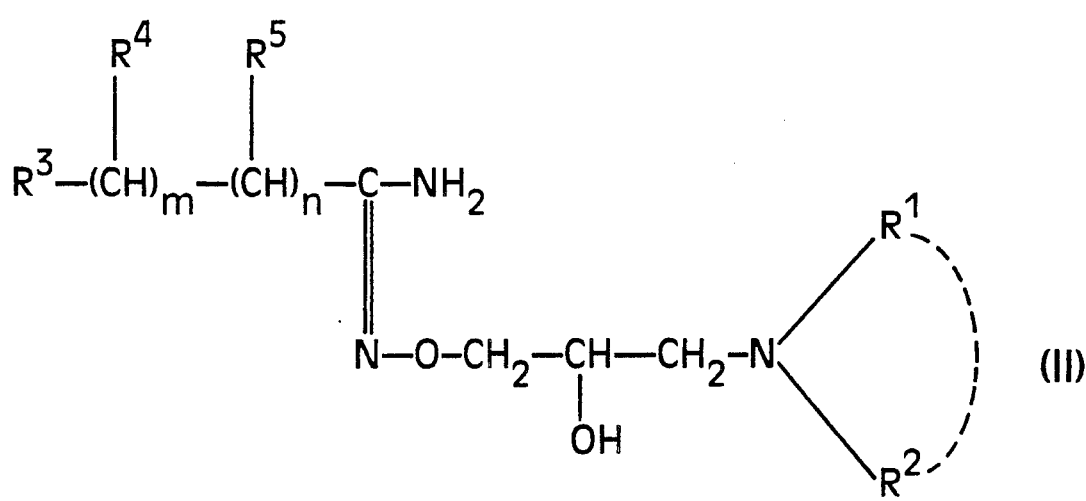
FIG. 2 is an amidoxim derivative represented by formula (II)
Figure 3:
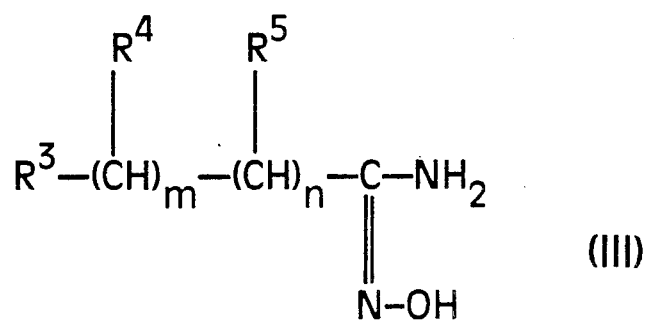
FIG. 3 is an aldoim represented by formula (III)
Figure 4:
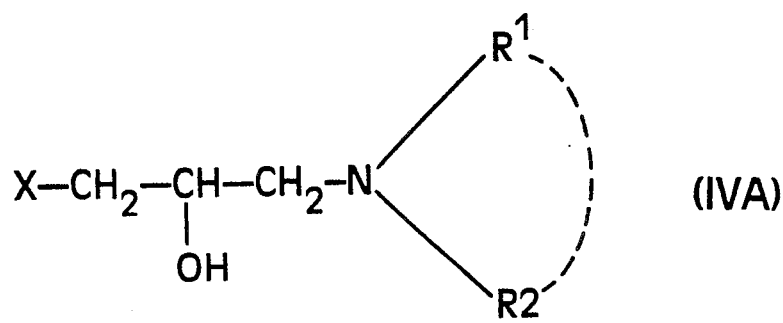
FIG. 4 is a base represented by formula (IV/A)
Figure 5:
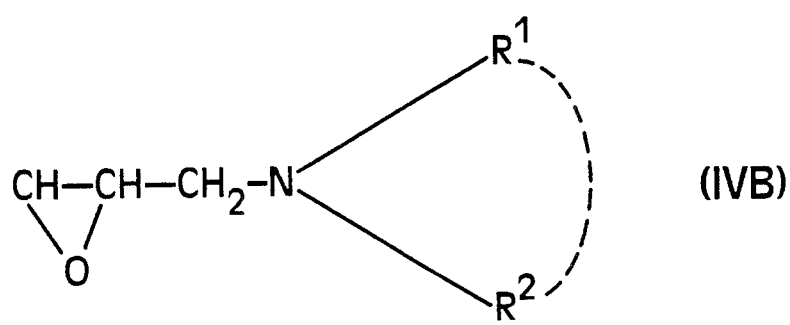
FIG. 5 is an amine represented by formula (IV/B)
Figure 6:
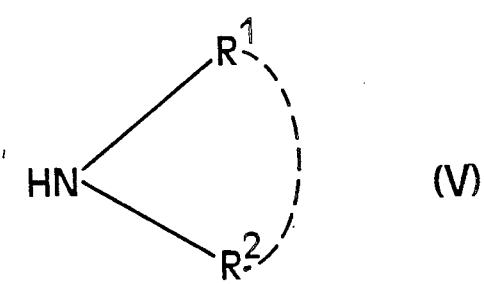
FIG. 6 is an amine represented by formula (V)
Figure 7:
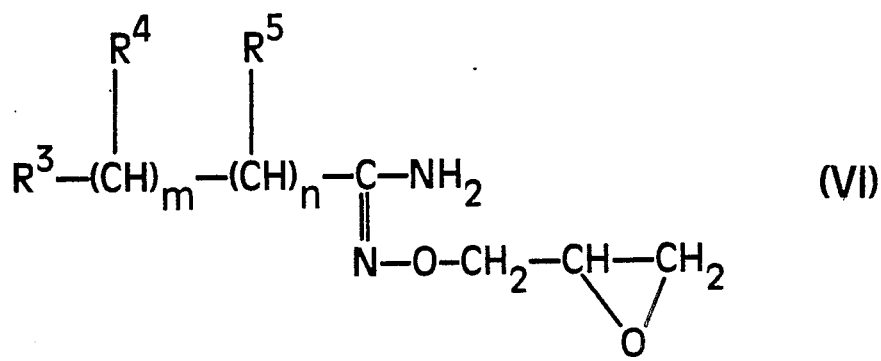
FIG. 7 is an aldoxim derivative represented by formula (VI)
Figure 8:
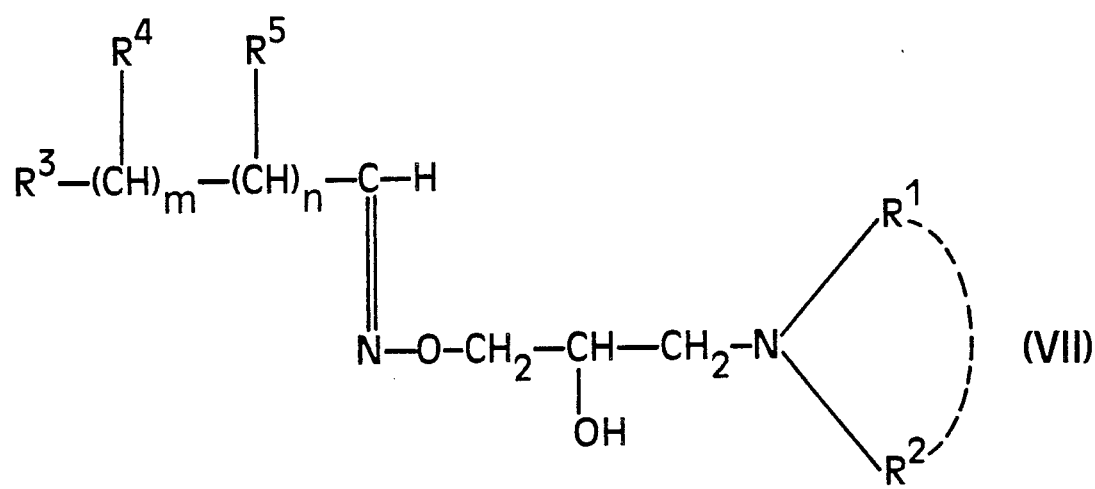
FIG. 8 is an aldoxim derivative represented by formula (VII)
Figure 9:
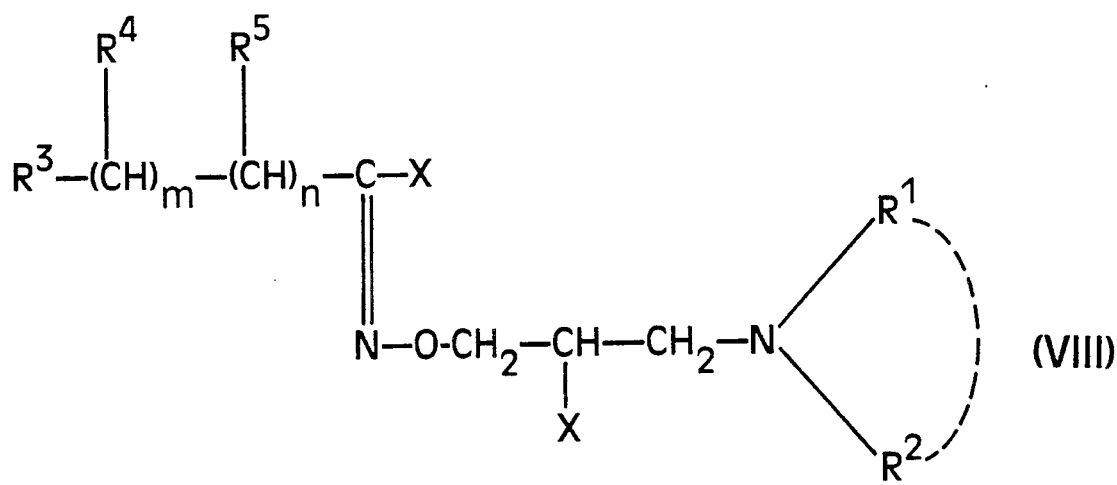
FIG. 9 is a halo derivative of a hydroximic acid represented by formula (VIII).

It has been found that the novel compounds of the formula (I) wherein

X is halo, such as fluoro, chloro, bromo and iodo.
$R^1$ is hydrogen of $C_{1-5}$ alkyl,
$R^2$ is $C_{1-5}$ alkyl, $C_{5-7}$ cycloalkyl or phenyl each optionally being substituted with hydroxy, and
$R^1$ and $R^2$, when taken together with the adjacent nitrogen atom, form a 5–8 membered ring optionally containing additional nitrogen and/or oxygen atom, which ring may also be condensed with a benzene ring, $R^3$ is hydrogen, phenyl, naphtyl or piridyl optionally substituted with one or more halo or alkoxy,
$R^4$ is hydrogen or phenyl,
$R^5$ is hydrogen or phenyl,
m is the integer of 0, 1 or 2 and
n is the integer of 0, 1 or 2, essentially do not influence, or only slightly, the adrenergic reactions of the healthy blood vessels, but show a strong effect on the adrenergic receptors deformed by the diabetes mellitus. This effect appears in the first line as a selective beta-blocking effect, consequently, the compounds of the general formula (I) are useful in medical influencing of diabetic angiopathy.

The common beta-blocking agents <Inderal, 1-(methyl-ethyl-amino)-3-(1-naphtalenyloxy)-2-propanol, Visken, 4,5-dihydro-2-(5-methyl-2-/1-methyl-ethyl-phenoxy/-methyl)-1H-imidazol> are contraindicated in the therapy of diabetic angiopathy.

Diabetes selective adrenergic receptor blocking compounds are described in Hungarian Patent No. 177,578, "Process for preparing novel OF-(3-amino-2-hydroxy-propyl)-amidoxim derivatives". Another object of the invention is the process for preparing the compounds of the general formula (I) and the salts thereof. According to the process a) an aldoxim of the general formula (III) wherein $R^3$, $R^4$, $R^5$, m and n are as defined above, is reacted in the presence of a base with an amine of the general formula (IV/A) and (IV/B), resp., wherein $R^1$ and $R^2$ are as defined above and X is halo, or b) an aldoxim of the general formula (III), wherein $R^1$, $R^2$ $R^3$, m and n are as specified above, is reacted with epichlorohydrine and the aldoxim derivative of the general formula (VI) thus obtained is reacted with an amine of the general formula (V), wherein $R^1$ and $R^2$ are as specified above, to obtain the aldoxim derivatives of the general formula (VII), and the compounds of the general formula (VII) according to the above processes a) or b) are reacted with inorganic acid halides, or other halogenating agents, e.g. $POX_3$, $SOX_3$, $PX_5$—wherein X is halo—to obtain the halo derivatives of the general formula (VIII), and by replacing the halo atom on the aliphatic chain thereof with hydroxy, the compounds of the general formula (I) are obtained, or c) an amidoxim derivative of the general formula (II) is diazotized in the presence of $NaNO_2$ and HX— wherein X is halo—and subjected to "boiling away" reaction.

If desired, the free bases of the general formula (I) may be transformed to acid addition salts by reacting with organic or inorganic acids, or the compounds obtained as salts may be transformed into the free bases.

According to a preferred embodiment of the process a) the reaction is carried out in aqueous medium, in an aqueous organic solvent, such as aqueous alcohol or in organic solvents, preferably at a temperature of 0° to 140° C.

According to an other embodiment of the process variant a) the salts of the aldoximes of the general formula (III) are formed in dry alcoholic medium with alkali alcoholates, and subsequently the solutions of the amines of the general formulae (IV/A) and (IV/B), resp., in alcohol are added thereto. The reaction is preferably carried out at a temperature of 0° to 100° C. under stirring.

According to a still another embodiment of the process variant a) the salts of the aldoximes of the general formula (III) are formed in a solvent non-miscible with water, such as benzene, toluene, xylene, with alkali hydroxides, preferably sodium or potassium hydroxide. The salt forming is carried out at the boiling temperature of the solvent, and the water forming during the reaction is continuously removed by azeotropic distillation, followed by the addition of the solution of the compounds of the general formulae (IV/A) and (IV/B), resp.

According to an other embodiment of the process variant a) the reaction is carried out in aqueous medium, by adding to the compounds (IV/A) or (IV/B) the aqueous-alkaline solution or suspension of the aldoximes under stirring.

The reaction is carried out preferably at a temperature of 0° to 6° C. and the aldoxim is added to the reaction mixture in the form of a solution or suspension of a temperature of 5° to 20° C. in aqueous alkali solution. The reaction may also be carried out in a mixture of water and an organic solvent, wherein to the solution of the compound of the general formula (IV/A) or (IV/B) in alcohol or dioxane the aqueous-alkaline solution or suspension of the aldoxim is added dropwise. The addition may also be accomplished in reversed order, i.e. to the aqueous-alkaline solution or suspension of the aldoxim is added the other reaction partner.

According to process variant b) the aldoxim of the general formula (III) is reacted with epichlorohydrine in the presence of a base. If desired, the epoxy compound obtained during the reaction may be isolated, it is preferred, however, to carry out the reaction in one synthesis step, without isolating the intermediate, in aqueous medium or in an organic solvent, aqueous organic solvent, or in a two-phase system, at a temperature of −10° to +60° C., by adding the reagent in one or two portions or dropwise. The order of addition may be reversed, i.e. either the alkaline solution or suspension aldoxim is added to the epichlorohydrine, or the aldoxim is added to the mixture of the epichlorohydrine and base. If desired, the intermediate of the formula (VI) may be separated by extracting with a solvent non-miscible with water. It is more preferred, however, to react the compound of the general formula (VI) without isolation with the corresponding amine.

The process variant b) may also be carried out in dry solvents, preferably dry alcohols. In this case the alkali metal salt of the aldoxim is formed, suitably by dissolving the aldoxim in a solution of alkali alcoholate in alcohol. Following the addition of the epichlorohydrine, the reaction mixture is allowed to stand for 1 to 5 days at a temperature of 0° to 20° C. and subsequently the reaction is carried on by the addition of the corresponding amine, at ambient temperature or by heating the mixture. Besides the alcohol, as dry solvent also other organic solvents, e.g. aceton, dimethyl sulfoxide, dimethyl formamide, etc. or the mixtures thereof may be used.

The compounds of the general formula (VII) obtained according to the processes a) or b) can be isolated by methods known per se. If aqueous medium is used, the isolation is generally accomplished by extraction, followed by drying and evaporating the solvent. Subsequently the aldoxim derivative of the formula (VII) is boiled with the inorganic acid halides, such as $PCl_5$, $SOCl_2$, $POCl_3$ for 1 to 5 hours in the presence or absence of a solvent, preferably halogenated solvents, such as $CHCl_3$. The compounds of the general formula (VII) thus obtained can be isolated by making the mixture alkaline with aqueous alkali, followed by extraction.

The compound of the general formula (VIII) is a hydroximic acid halogenated in the chain. It has been found that the halo moiety thereof will not enter into nucleophylic substitution reaction under the reaction conditions, and accordingly, the formation of the OH group will be accomplished selectively, in one step by aqueous-alkaline hydrolysis at a temperature of 0° to 100° C., using preferably alkali hydroxides or other metal hydroxides, e.g. silver hydroxide, or in two steps, first forming an ester moiety suitably with the alkali salts of lower carboxylic acids followed by the hydrolysis to obtain the compounds of the general formula (I).

The reaction conditions of process variant c) are selected so that the temperature is maintained between −5° and +10° C. and thus, also the "boiling away" reaction takes place. Preferably the reaction is carried out in water, and the intermediate diazonium salt is not isolated but also the "boiling away" reaction is carried out by selecting suitable reaction conditions thus obtaining the compounds of the general formula (I).

The reaction products can be separated from the reaction mixture by methods known per se, e.g. by crystallisation and extraction, when using water as reaction medium. When organic solvents are used, crystallisation or evaporation followed by washing with water and extraction is applied. The products may be isolated in the form of salts thereof, or from the isolated bases salts may be formed by using molar equivalent of mineral or organic acids, preferably pharmaceutically acceptable acids, or, if desired, from the salts the free bases can be obtained.

The general beta-blocking effect of the compounds of the general formula (I) was studied on anaesthetised cats. In these tests besides registering the blood pressure and pulse rate, also the effect of the test materials on the left ventricular contractility was studied. As reference material Inderal <1-isopropylamino-3-(naphtyloxy)-propan-2-ol> was used.

The beta-blocking effect of the compounds according to the present invention was tested on rat aorta spiral and/or ring preparate <J. Pharmacol. Exp. Therap. 158, 531 (1967)>. The experimental diabetes was induced with Streptosotocin <2-(3-nitroso-3-methylureido)-2-deoxy-D-glucose>. The reaction was evaluated as positive when the alpha stimulating effect of the noradrenalin on the control preparate, i.e. that having not been treated with Streptosotocin, was not influenced, but protected on the diabetic aorta. In the tests carried out with the compounds according to the present invention a general selective effect occurred, manifesting in case of diabetic tests in a strong, in case of normal tests in the absence of or in the presence of only a slight beta-blocking effect.

Experiments were carried out to study whether on the aorta spiral preparates of diabetic animals treated with Streptosotocin the Inderal protects the contractions induced by noradrenalin. As control, animals previously not treated with Streptosotocin were used. The results obtained essentially conformed to those known from the literature <Amer. J. Physiol., 218, 869 (1970)>, i.e. the alpha stimulating effect of noradrenalin was protected by the Inderal in diabetic tests, but not in the normal tests. (Endocrinology. Vol. 93, No. 3, September 1973).

It has been found that the compounds of the general formula (I) showed a slight general beta-blocking effect. Compared with the control beta-blocking Inderal the compounds tested showed an effect of two orders of magnitude less in the inhibition of the beta-blocking D,L-1-(3,4-dihydroxy-phenyl)-2-isopropylamino-ethanol.

At the same time the compounds of the general formula (I) produced a significant parallel shift to the right of the noradrenalin dose-response curve in diabetic rat aorta ring (and/or spiral) in the order of magnitude of the effect of Inderal. The dose of Inderal was 0,5 micrograms/ml, while the dose of the compounds of the general formula (I) was 1,0 microgram/ml.

Accordingly, the O-(3-amino-2-hydroxypropyl)-hydroximic acid halides of the general formula (I) may preferably be used in the therapy of any kind of diabetic micro- and macroangiopathy, especially of diabetic retinopathy and diabetic nephropathy in case of diabetes mellitus. The above compounds can be used per se or in the form of pharmaceutical preparations. The above treatment and pharmaceutical compositions also form the object of the present application. The pharmaceutical compositions of the present invention can be used for prevention, for treatment in the active phase of the disease as well as in acute cases.

The hydroximic acid halides of the general formula (I) are effective exclusively on patients in the stadium of formation of diabetes, and are ineffective on non-diabetic persons.

BEST MODE OF CARRYING OUT THE INVENTION

Preferred are those compounds of the general formula (I) wherein X is chloro, m and n are each 0, $R^3$ is 3,4-dimethoxybenzyl, piridyl, napthyl or indolyl and $R^1$ is and $R^2$ is isopropyl, 2-hydroxyethyl or t-butyl, or $R^1$ and $R^2$ together form pentamethylene. Especially preferred active compounds are those mentioned in the following examples.

The invention is further illustrated in the following examples. It is to be understood, however, that the scope of protection is not limited to the matter disclosed in the examples any way.

EXAMPLE 1

2,3 g of sodium were dissolved in 200 ml of abs. ethanol and then 12,1 g of benzaldoxim were added. At boiling temperature the solution of 3-piperidino-2-hydroxy-1-chloropropane prepared from 9,3 g epichlorohydrine and 8,5 g of piperidine in 50 ml of abs. ethanol by methods known per se was added dropwise. The reaction mixture was boiled for 8 hours under reflux, the precipitated salt was filtered at room temperature and the solvent was distilled off in vacuo. To the residue 100 ml of 5% sodium hydroxide were added and the oily product was extracted with benzene. After drying and evaporating the benzene extract 8,2 g of O-(3-piperidino-2-hydroxy-1-propyl)-benzaldoxim was obtained. The hydrochloride of the product was separated from the isopropanol solution thereof by introducing gaseous hydrochloric acid into or adding hydrochloric acid in ethanol to the solution. Mp. 137° C. (from isopropanol).

Analysis based on $C_{15}H_{23}ClN_2O_2$: Mw. 298,81 Calculated: C 60,29, H 7,76, N 9,37, Cl 11,86; Found: C 60,35, H 8,00, N 9,25, Cl 11,90%.

2,98 g of O-(3-piperidino-2-hydroxy-1-propyl)-benzaldoxim were boiled in 20 ml of thionyl chloride for 3 hours. The O-(3-piperidino-2-chloro-1-propyl)-benzhydroximic acid chloride was separated by adding about 100 ml of 20% aqueous base until pH=11 followed by extraction with chloroform. The chloroform extract was dried over sodium sulfate and evaporated. The oil-like product can be transformed into the compound of the general formula by different ways:

a) 3,4 g of oily product were hydrolized with 20 ml of 20% NaOH at 55° to 60° C. for 2 hours under stirring, extracted with benzene, the benzene solution was dried with solid drying agent and subsequently evaporated. To the residue 50 ml of hydrochloric acid in ethyl acetate was added. Under stirring the hydrochloride of the O-(3-piperidino-2-hydroxy-1-propyl)-benzhydroximic acid chloride precipitated.

Yield: 2,1 g. NMR (base, $CDCl_3$): 7,4–8,0 m (5H); 3,9–4,4 m (3H); 2,2–2,8 m (6H); 1,3–1,8 m (6H); 3,5 s (OH). Mp. 140°–142° C. (from isopropanol)

Analysis: based on $C_{15}H_{22}Cl_2N_2O_2$ Calculated: C 54,22, H 6,37, H 8,43, Cl 21,14; Found: C 53,12, H 6,26, H 8,19, Cl 20,84%.

b) 0,81 g (4,74 mmoles) of $AgNO_3$ were dissolved in 4 ml of water and under stirring 0,19 g of NaOH (4,74 mmoles) in 3 ml of water was added thereto dropwise. The aqueous suspension of the AgOH precipitate was stirred with 1,5 g (4,74 mmoles) of O-(3-piperidino-2-chloro-1-propyl)-benzhydroximic acid chloride at 50° C. for 3 hours. Then the suspension was extracted with benzene, the benzene layer was dried with sodium sulfate, filtered, evaporated and subjected to the salt forming step described in process a). Yield 95%. The physical data of the end product are identical with those in process a).

c) 3,0 g (9,49 mmoles) of O-(3-piperidino-2-chloro-1-propyl)-benzhydroximic acid chloride were dissolved in 10 ml of ethanol, under stirring 0,86 g (1,05.10$^{-2}$ moles) of sodium acetate in 15 ml of water were added and the mixture was stirred for 3 hours at 50° C. The reaction mixture was evaporated in vacuo and the residue was extracted with benzene. The benzene extract was dried over sodium sulfate and evaporated, thus providing 2,12 g of oily O-(3-piperidino-2-acetoxy-1-propyl)-benzhydroximic acid chloride. The ester thus obtained was dissolved in 20 ml of ethanol followed by the addition of 20 ml of water. 0,25 g of NaOH in 20 ml of water were added to the mixture and stirred at 40° C. for one hour, extracted with benzene, the benzene extract was dried with sodium sulfate and evaporated. From the residue salt was formed according to the method in process a). Yield 90%. The quality of the product was identical with that of process a).

EXAMPLE 2

Following the process as described in Example 1 but starting from 3-piridyl-aldoxim and 3-piperidino-2-hydroxy-1-chloropropane the O-(3-piperidino-2-hydroxy-1-propyl)-3-piridylaldoxim was prepared, which was reacted with thionyl chloride according to Example 1. After removing the thionyl chloride by evaporation, isopropanol was added to the residue thus crystallising the O-(3-piperidino-2-chloro-1-propyl)-3-piridyl-hydroximic acid chloride in the form of the dihydrochloride Mp. 142° C. (from isopropanol). Yield 85%.

Analysis based on $C_{14}H_{21}Cl_4N_3O$: Mw=389,15 Calculated: C 43,21, H 5,44, N 10,79, Cl 36,44; Found: C 42,97, H 5,62, N 10,59, Cl 36,80%.

According to another mode of preparation the O-(-3-piperidino-2-chloro-1-propyl)-3-piridyl-hydroximic acid chloride dihydrochloride obtained as above was not isolated, instead, to the evaporation residue 10% NaOH was added until a pH of 11 in accordance with Example 1 and the mixture thus obtained was extracted with chloroform. The chloroform layer was dried, evaporated and subsequently hydrolized by using any of the processes a), b) and c) of Example 1. The hydrolysis mixture was extracted with benzene, dried with sodium sulfate and evaporated. The residue was dissolved in aceton followed by the addition of maleic acid and isolating the O-(3-piperidino-2-hydroxy-1-propyl)-3-piridyl-hydroximic acid chloride maleate thus obtained by filtering. NMR (base, CDCl$_3$): 9,03, 8,59, 8,00, 7,1–7,4, 3,84 s (3H), 1,1–1,8 (6H), 5,28 s (OH). Mp. 125° C. (from aceton). Yield 65%.

Analysis based on $C_{18}H_{24}ClN_3O_6$: Mw.=413,79 Calculated: C 52,24, H 5,84, N 10,15, Cl 8,55; Found: C 52,26, H 5,99, N 9,87, Cl 8,46%.

EXAMPLE 3

To 3,5 g (10 mmoles) of O-(3-piperidino-2-hydroxy-1-propyl)-benzamidoxim dihydrochloride 40 mmoles of hydrogen chloride (in 37% form) was added at 5° C. under vigorous stirring. After the addition of 5 ml of dioxane the mixture was cooled to 0° C. by using salt-ice. At the same temperature a solution of 1,38 g (20 mmoles) of NaNO$_2$ in 6 ml water was added dropwise during a period of 1,5 hours followed by intensive stirring for 4 hours at ambient temperature. The acidic reaction mixture was made alkaline by the addition of 10% sodium hydroxide until a pH of 11 and then extracted with 80 to 100 ml of benzene. The benzene layer was dried over sodium sulfate and evaporated. From the residue the hydrochloride of the O-(3-piperidino-2-hydroxy-1-propyl)-benzhydroximic acid chloride was formed by the addition of a saturated solution of hydrochloric acid in ethyl acetate and isolated by filtering. Mp. 139°–141° C.

Analysis based on $C_{15}H_{22}Cl_2N_2O_2$: Mw=333,25 Calculated: C 54,22, H 6,37, N 8,43, Cl 21,14; Found: C 54,62, H 6,16, N 8,09, Cl 20,71%.

EXAMPLE 4

The process described in Example 3 was followed but instead of hydrochloric acid, hydrogen bromide was used as hydrogen halide, thus obtaining the O-(3-piperidino-2-hydroxy-1-propyl)-benzhydroximic acid bromide hydrochloride. Yield 27%. Mp. 138° C. (from isopropanol)

Analysis based on $C_{15}H_{22}BrClN_2O_2$: Mw=377,71 Calculated: C 47,63, H 5,87, N 7,41; Found: C 47,60, H 6,19, N 7,50%.

EXAMPLE 5

Following the process as described in Example 3 O-(3-piperidino-2-hydroxy-1-propyl)-nicotinic acid amidoxim dihydrochloride was diazotized, by using hydrochloric acid as hydrogen halide. Following the diazotizing and "boiling away" reaction from the O-(3-piperidino-2-hydroxy-propyl)-3-piridyl-hydroximic acid chloride the maleate was formed in dry organic solvent by adding molar equivalent of maleic acid, and then separated. Mp. 125° C. (from aceton). Yield 58%.

Analysis based on $C_{18}H_{24}ClN_3O_6$: Mw=413,79 Calculated: C 52,24, H 5,84, N 10,15, Cl 8,55; Found: C 52,26, H 5,99, N 9,87, Cl 8,46%. LD$_{50}$: 110 mg/kg iv. on Wistar rats.

EXAMPLE 6

Following the process as described in Example 5 but using hydrogen bromide instead of the hydrochloric acid as hydrogen halide, the O-(3-piperidino-2-chloro-1-propyl)-3-piridyl-hydroximic acid bromide maleate was obtained Yield. 58%, Mp. 117° C. (from aceton)

Analysis based on $C_{18}H_{24}BrN_3O_6$: Mw=457,25 Calculated: C 47,36, H 5,21, N 9,16, Br 17,13; Found: C 47,67, H 5,31, N 8,80, Br 16,78%.

EXAMPLE 7

Following the process as described in Example 3 but using O-(3-piperidino-2-hydroxy-1-propyl)-3,3-diphenyl-propionic acid hydroximic acid dihydrochloride as amidoxim component in the diazotizing reaction, the O-(3-piperidino-2-hydroxy-1-propyl)-3,3-diphenyl-propionic acid hydroximic acid dihydrochloride was obtained.

Yield: 30%. Mp. 149°–152° C. (from isopropanol).

NMR (base, DMSOd$_6$): 7,1–7,6 m (10H), 4,5 t (14), 3,34 d (2H), J=7,5 Hz, 3,9 br s (3H), 2,3–3,0 m (6H), 1,3–1,9 m (6H), OH shaded.

Analysis based on $C_{23}H_{30}Cl_2N_2O_{22}$: Mw=437,40 Calculated: C 63,15, H 6,51, N 6,40, Cl 16,21; Found: C 63,50, H 6,79, N 6,31, Cl 16,47%.

EXAMPLE 8

Following the process as described in Example 3 but using O-(3-diethylamino-2-hydroxy-1-propyl)-3,3-diphenyl-propionic acid amidoxim dihydrochloride as starting amidoxim component, the O-(3-diethylamino-2-hydroxy-1-propyl)-3,3-diphenyl-propionic acid hydroximic acid chloride dihydrochloride was obtained. Yield: 32%. Mp. 155° C. (from isopropanol).

Analysis based on $C_{22}H_{30}Cl_2N_2O_2$: Mw=425,40 Calculated: C 62,11, H 7,10, N 7,52, Cl 16,66; Found: C 62,10, H 6,98, N 7,45, Cl 17,00%.

EXAMPLE 9

Following the process as described in Example 3 but using O-(3-isopropylamino-2-hydroxy-1-propyl)-benzamidoxim dihydrochloride as starting amidoxim component, the O-(3-isopropylamino-2-hydroxy-1-propyl)-benzhydroximic acid hydrochloride was prepared. Yield 12%. Mp. 122° C. (from isopropanol).

Analysis based on $C_{13}H_{20}Cl_2N_2O_2$: Mw=307,22 Calculated: C 50,82, H 6,56, N 9,11, Cl 23,08; Found: C 51,12, H 6,58, N 9,05, Cl 22,89%.

EXAMPLE 10

N-[2-hydroxy-3-(piperidin-1-yl)-propoxy]-2-pyridincarboximidoyl chloride (Z)-2-butendioate (1:1)

The process of example 3 was repeated but using O-(2-hydroxy-3-(piperidin-1-yl)-propyl-carboxamide-oxime dihydrochloride as amidoxim component and isolating the product as maleate in acetone medium. Yield 1,3 g (31%), Mp.: 61°–64° C. (from ethyl acetate).

TLC: $R_f$=0,67 (Kieselgel 60, eluent: PhMe-MeOH-EtOAc-cc.NH$_4$OH 7:6:6:1).

IR: ([cm$^{-1}$]/KBr): 3416, 1670, 1574, 1506, 1367, 1055, 997, 991, 864, 791, 717.

$^1$HNMR (250 MHz, DMSO; referent DMSO=2,50 [ppm]): 8,70 d, 1H, 7,90 b,2H, 7,53 m,1H (pyridin 6-3/4-5-), 6,03 s,2H (CH=CH), 4,32 bs,3H (NOCH$_2$+CHOH), 3,3–3,0 b, 6H (3×NCH$_2$), 1,75 b, 4H [2×CH$_2$(3)]1,54 b,2H [CH$_2$(4)].

$^{13}$C-NMR (63 MHz, DMSO; referent DMSO=39,3 [ppm]): 166,8, 148,5, 125,1, 136,8, 121,7 149,1 (pyridin 2-3-4-5-6), 135,3 (CH=CH), 137,8 (C(Cl)=N), 76,9 (NOCH$_2$), 63,0 (CHOH), 57,9 (CH—CH$_2$—N), 52,6 [CH$_2$(2)], 21,9 [CH$_2$(3)], 20,8 [CH$_2$(4)].

EXAMPLE 11

N-[2-hydroxy-3-(diethyl-amino)-propoxy]-3-pyridinecarboximidoyl chloride hydrochloride (1:1)

To a solution of 1,0 g (3,7 mmole) N-[2-hydroxy-3-diethyl-amino-propoxy]-3-pyridinecarboximide-amide (CAS [131782-74-6], CA 90 435907) in 5 ml water and 1,8 ml cc. HCl at 5 to 0° C. the solution of 0,81 g NaNO$_2$ (11,7 mmole) in 3 ml water was added dropwise and the mixture was stirred for 1 hour at the same temperature. Then 0,78 g NaOH in 4 ml water was added and the product was extracted with 2×10 ml of ether. The ether solution was washed with 3×10 ml water, dried over Na$_2$SO$_4$ and evaporated. The oily residue (0,53 g) was dissolved in 5 ml isopropanol and the product was precipitated by the addition of 4M HCl/iPrOH. Yield: 0,35 g (29%). M.p.: 117°–118° C.

TLC: $R_f$=0,66 (Kieslgel 60, eluent: PhMe-MeOH-EtOAc-cc.NH$_4$OH 7:6:6:1).

IR: ([cm$^{-1}$]/KBr): 3292, 2959, 2854, 1578, 1475, 1484, 1409, 1273, 1099, 1049, 976, 901, 833, 704.

$^1$H-NMR (250 MHz, DMSO, referent DMSO=2,50 [ppm]): 10,35 b, 1H (NH$^+$), 8,97 d, 8,70 dd, 8,17 m, 7,55 m (pyridin 2-6-4-5-), 6,02 d, 1H (OH), 4,45–4,25 m,3H (NOCH$_2$+CHOH), 3,4–3,0 m,6H (3×NCH$_2$), 2,25 t,6H (2×CH$_3$).

$^{13}$C-NMR (63 MHz, CDCl$_3$, referent CDCl$_3$=77,0 [ppm]): 151,0, 128,6, 134,3, 123,1, 148,0 (pyridin 2-3-4-5-6), 135,2 [C(Cl)=N), 78,2 (NOCH$_2$), 65,5 (CHOH), 55,5 (CH—CH$_2$—N), 47,1 (CH$_2$—CH$_3$), 11,8 (CH$_3$).

EXAMPLE 12

N-[2-hydroxy-3-(pyrrolidin-1-yl)-propoxy]-3-pyridincarboximidoyl chloride (Z)-2-butendioate (1:1).

N-[2-hydroxy-3-(pyrrolidin-1-yl)-propoxy]-3-pyridincarboximid-amide dihydrochloride (CAS [131782-78-0], CA 90 435907) was diazotized according to example 15. The product was isolated in the form of maleate from ethyl acetate. Yield 0,3 g (25%). M.p.: 89°–92° C.

TLC: $R_f$=0,58 (Kieselgel 60, eluent: PhMe-MeOH-EtOAc-cc.NH$_4$OH 7:6:6:1).

IR ([cm$^{-1}$]/KBr): 3323, 2953, 1585, 1497, 1385, 1366, 1194, 1070, 1022, 876, 864, 704.

$^1$H-NMR (250 MHz, DMSO; refent DMSO=2,50 [ppm]; T 333K 8,97 d, 8,69 dd, 8,15 m, 7,53 m (pyridin 2-6-4-5), 6,03 s,2H (CH=CH), 4,4–4,2 m, 3H (NOCH$_2$+CHOH), 3,4–3,1 m, 6H (3×NCH$_2$), 1,9 bs, 4H (2×CH$_2$).

$^{13}$C-NMR (63 MHz, DMSO; referent DMSO=39,3 [ppm]): 166,8 (COOH), 151,3, 127,5, 134,2, 123,5, 147,0 (pyridin 2-3-4-5-6), 135,6 (CH=CH), 134,6 [C(Cl)=], 64,2 (CHOH), 55,9 (CH—CH$_2$—N), 53,6 (NCH$_2$), 22,1 (CH$_2$).

EXAMPLE 13

Following the processes described in the previous examples the following compounds were prepared:

N-[2-hydroxy-3-(2,6-dimethyl-piperidin-1-yl)-propoxy]-3-pyridincarboximidoyl chloride M.p.: 78,5°–79° C. (iPr$_2$O)

TLC: $R_f$=0,66 (Kieselgel 60, eluent: PhMe-MeOH-EtOAc-cc.NH$_4$OH 7:6:6:1)

IR ([cm$^{-1}$]/KBr): 3090, 2930, 1580, 1435, 1379, 1307, 1275, 1204, 1094, 1049, 1020, 980, 914, 714.

$^1$HNMR (250 MHz, CDCl$_3$, referent TMS=0,0 [ppm]): 9,09 d, 8,66 dd, 8,12 m, 7,35 m (pyridin 2-6-4-5-), 4,33 d, 2H (NOCH$_2$); 2,6 m,2H (2×NCH), 1,8–1,2 m,6H (3×CH$_2$, 1,12 d,6H (2×CH$_3$).

$^{13}$-NMR (63 MHz, CDCl$_3$, referent CDCl$_3$=77,0 [ppm]): 151,0, 128,7, 134,3, 123,0, 148,0 (pyridin, 2-3-4-5-6), 135,1 [C(Cl)=N), 78,5 (NOCH$_2$), 66,9 (CHOH), 55,2 (NCH$_2$), 59,3 and 57,7 (2×CH), 33,2 and 32,9 &2×CH$_2$(3)], 24,1 [CH$_2$(4)], 21,9 and 21,6 (2×CH$_3$).

N-[2-hydroxy-3-(morpholin-1-yl)-propoxy]-3-pyridin-carboxamidoyl chloride (Z)-2-butendioate (1:1)

M.p.: 137°–138° C.

TLC: $R_f$=0,45 (Kieselgel 60, eluent: PhMe-MeOH-EtOAc-cc.NH$_4$OH 7:6:6:1).

IR ([cm$^{-1}$]/KBr): 3310, 1580, 1483, 1464, 1443, 1354, 1072, 1024, 982, 870.

$^1$H-NMR (250 MHz, DMSO; referent DMSO=2,50 [ppm]; 9,00 d, 8,72 dd, 8,18 dd, 7,57 m (pyridin 2-6-4-5), 6,03 s,2H (CH=CH), 5,9 b, 1H (OH), 4,2–4,3 b, 3H (NOCH$_2$+CHOH), 3,80 d, 4H (2×OCH$_3$), 3,0–3,3 b,6H (3×NCH$_2$).

$^{13}$C-NMR (63 MHz, DMSO; referent DMSO=39,3 [ppm]): 167,0 (COOH), 151,5, 127,8, 134,4, 123,7, 147,2 (pyridin 2-3-4-5-6), 135,2 (CH=CH), 134,2 [C(Cl)=N], 77,1 (NOCH$_2$), 63,1 (CHOH), 58,4 (CH$_2$—N), 63,2, 51,7 (morpholin).

N-[2-hydroxy-3-(4-methyl-piperazin-1-yl)-propoxy]-3-pyridincarboximidoyl chloride (Z)-2-butendioate (1:2).

M.p.: 174°–175° C.

TLC: $R_f$=0,51 (Kieselgel 60, eluent: PhMe-MeOH-EtOAc-cc.NH$_4$OH 7:6:6:1).

IR ([cm$^{-1}$]/KBr): 3207, 1693, 1578, 1456, 1358, 1304, 1020, 974, 864, 702.

$^1$H-NMR (250 MHz, DMSO, referent TMS=0,0 [ppm]; 8,97 d, 8,72 dd, 8,17 m, 7,56 m (pyridin 2-6-4-5), 6,15 s,4H (CH=CH), 4,3 m,2H (NOCH₂) 4,05 m,1H. (CHOH), 3,25–2,5 m, 16H (5×NCH₂, NCH₃, 2×NH+, OH), 11–14 b (2×COOH).

¹³C-NMR (63 MHz, DMSO; referent DMSO=39,3 [ppm]): 166,8 (COOH), 151,3, 127,9, 134,3, 123,7, 147,1 (pyridin 2-3-4-5-6), 134,2, [C(Cl)=N], 133,2, (CH=CH), 78,0 (NOCH₂), 65,7 (CHOH), 59,1 (CH—CH₂—N), 55,2, 50,0 (NCH₂), 42,3 (CH₃).

N-[2-hydroxy-3-prop-2-yl-amino)-propoxy]-3-pyridin-carboximidoyl chloride (Z)-butendioate (1:1)
M.p.: 108°–109,5° C.

TLC: R$_f$=0,55 (Kieselgel 60, eluent: PhMe-MeOH-EtOAc-cc.NH₄OH 7:6:6:1).

IR ([cm⁻¹]/KBr): 3200 (b), 1582, 1479, 1383, 1358, 1200, 1119, 1057, 986, 876, 700.

¹H-NMR (250 MHz, DMSO; referent DMSO=2,50 [ppm]; 9,08 d, 8,72 dd, 8,17 m, 7,57 m (pyridin 2-6-4-5); 8,40 b,2H (NH₂⁺), 6,02 s, 2H (CH=CH), 5,9 b, 1H (OH), 4,30 d,2H (NOCH₂), 4,19 b,1H (CH—OH), 3,10 m,1H és 2,9 m, 1H (NCH₂), 3,35 m, 1H és 1,23 d, 6H (izopropil).

¹³C-NMR (63 MHz DMSO; referent DMSO=39,3 [ppm]): 167,1 (COOH), 151,5, 127,7, 134,3, 123,7, 147,1 (pyridin 2-3-4-5-6), 135,9 (CH=CH), 134,8 [C(Cl)=N], 76,7 (NOCH₂); 64,8 (CHOH), 49,7 (NCH₂), 46,2, 18,6 és 17,9 (izopropil).

N-[2-hydroxy-3-(tert-butyl-amino)-propoxy]-3-pyridin-carboxamidoyl chloride (Z)-2-butenoate (1:1)
M.p.: 148,5°–149° C.

TLC: R$_f$=0,51 (Kieselgel 60, eluent: PhMe-MeOH-EtOAc-cc.NH₄OH 7:6:6:1).

IR ([cm⁻¹]/KBr): 3500-2700 (b), 2986, 1632, 1582, 1470, 1356, 1204, 1124, 1067, 1034, 997, 874, 698.

¹H-NMR (250 MHz, DMSO; refent DMSO=2,50 [ppm]; 12,4 b, 1H (COOH), 8,98 d, 8,72 dd, 8,17 m, 7,58 m (pyridin 2-6-4-5-), 8,35 b, 2H (NH₂⁺), 6,03 s,2H (CH=CH), 5,9 b, 1H (OH), 4,33 d,2H (NOCH₂), 4,19 b, 1H (CHOH), 3,10 b, 1H és 2,88 m, 1H (NCH₂), 1,3 s,9H (3×CH₃).

¹³C-NMR (63 MHz, DMSO; referent DMSO=39,3 [ppm]): 167,0 (COOH), 151,5, 127,5, 134,3, 123,7, 147,1 (pyridin 2-3-4-5-6), 135,8 (CH=CH), 134,6 [C(Cl)=N], 76,6 (NOCH₂), 64,7 (CHOH), 56,2 (CH₂—N), 43,4, 24,8 (butyl).

N-[2-hydroxy-2-(cyclohexyl-amino)-propoxy]-3-pyridin-carboximidoyl chloride (Z)-2-butendioate (1:1)
Mp.: 135,5°–136,5° C.

TLC: R$_f$=0,64, Kieselgel 60, Eluent PhMe-MeOH-EtOAc-cc.NH₄OH 7:6:6:1.

IR [cm⁻¹]/KBr: 3500-2700 (b), 2943, 1590, 1454, 1350, 1200, 1040, 1003, 989, 872, 737, 714.

¹HNMR (250 MHz, DMSO; referent DMSO=2,50 [ppm]): 8,98, d, 8,72 dd, 8,17 m, 7,57 m, 1H (pyridin 6-3/4-5-), 8,4 b, 2H (NH₂⁺, 6,03 s,2H (CH=CH); 5,87 b, 1H (OH), 4,328 d, 2H (NOCH₂), 4,22 m, 1H (CH—OH), 3,2–2,9 m, 3H (NCH₂+NCH), 2,15–1,0 m,10H (5×CH₂).

¹³C-NMR (63MHz, DMSO; referent DMSO=39,3 [ppm]): 167 (COOH) 151,5 127,7, 134,3; 123,7, 147,1 (pyridin 2-3-4-5-6), 135,8 (CH=CH), 134,8 (C(Cl)=N), 76,7 (NOCH₂), 64,7 (CHOH), 56,1 (CH₂—N), 45,9 (N—CH₃), 28,5 and 27,8 [2×CH₂(2)], 24,5 and 23,8 [2×CH₂(3)], 23,7 [CH₂(4)].

N-[2-hydroxy-3-(5,6-dimethoxy-1,2,3,4-tetrahydro-isoquinolin-2-yl]-propoxy]-3-pyridin-carboximidoyl chloride
Mp.: 111,5°–112° C.

TLC: R$_f$=0,50, Kieselgel 60, Eluent CHCl₃-MeOH 9:1).

IR [cm⁻¹]/KBr: 3132 (b), 2949, 2812, 1580, 1514, 1488, 1384, 1289, 1225, 1128, 1053, 994,922, 845, 810, 710, 700.

¹HNMR (250 MHz, CDCl₃; referent TMS=0,0 [ppm]): 9,08 d, 8,65 d, 8,12 d, 7,35 m (pyridin 6-3-4-5-), 6,63 s, 6,53 s (Ph), 4,38 d, 2H (NOCH₂), 4,22 m, 1H (CH—OH), 3,65 ABq, 2H (NCH2), 3,83 (2×s, 6H (2×CH₃), 3,0–2,6 m, 6H (3×CH₂).

¹³C-NMR (63 MHz, CDCl₃; referent CDCl₃=77,0 [ppm]): 151,1, 128,6, 134,4, 123,1, 148,0 (pyridin 2-3-4-5-6), 147,6, 147,2, 126,0, 125,8, 111,3, 109,3 (Ph), 135,4 (C(Cl)=N), 78,1 (NOCH₂), 65,7 (CHOH), 60,0 (CH₂—N), 55,8 (OCH₃), 55,6 (N—CH₂—Ph), 51,1 (N—CH₂—CH₂), 28,5 (CH₂—CH₂—Ph).

EXAMPLE 14

N-[2-hydroxy-3-(1-piperidyl)-propoxy]-α-(3,4-dimethoxy-phenyl)-acetimidoyl chloride 3,87 g (10 mmoles) N-[2-hydroxy-3-(1-piperidyl)-propoxy]-α-(3,4-dimethoxy-benzyl)-acetamidin hydrochloride (CAS [131782-83-7]) was dissolved in 15 ml water. The solution was cooled to −4°/−5° C., 3,8 ml HCl was added thereto and a solution of 2,76 g(40 mmoles) NaNO₂ in 8 ml water was added dropwise at the same temperature. The mixture was stirred at the same temperature for additional 2 hours and subsequently made alkaline by the addition of 2 g NaOH/8 ml water. The product was extracted with 3×15 ml benzene, the benzene solution washed with 15 ml water and 15 ml saturated NaCl solution, dried over Na₂SO₄ and evaporated.

The 2,9 g oily residue was dissolved in 10 ml ethyl acetate, acidified with HCl in ethyl acetate to pH=2 and evaporated. By treating the oil with 20 ml acetone 0,4 g solid, unreacted starting material was recovered.

The acetone filtrate was evaporated, the residue was dissolved in 15 ml water. The pH was adjusted to 8 with NaHCO₃ followed by extraction with 3×10 ml ethyl acetate. The organic solution was washed with 1×10 ml water, dried over Na₂SO₄ and evaporated. The crude product was subjected to chromatography on 60 g Kieselgel 60 with acetone-ethyl acetate (1:1) mixture. Yield: 1,02 (27,5%) colorless oil.

TLC: R$_f$=0,80, Kieselgel 60, Eluent PhMe-MeOH-EtOAc-cc.NH₄OH 7:6:6:1.

IR [cm⁻¹]/film: 3400 (b), 2930, 1605, 1590, 1515, 1460, 1260, 1235, 1145, 1020, 980, 845, 745, 655.

¹HNMR (250 MHz, CDCl₃; referent TMS=0,0 [ppm]): 6,82 s,2H and 6,77 s,1H (phenyl), 4,17 m,2H (NOCH₂), 4,05 m, 1H (CH) 3,86 2×s,6H (2×OCH₃), 3,71 s,2H (Ph—CH₂), 3,6 b, 1H (OH), 2,38 d, 2H (CH₂—CH₂—N), 2,58 m, 2H, 2,37 m,2H, 1,56 m,4H and 1,45 m, 2H (piperidine).

¹³C-NMR (63 MHz, CDCl₃; referent CDCl₃=77,0 [ppm]): 149,0, 148,3, 127,1, 121,3, 112,1 and 111,2 (phenyl), 139,1 [C(Cl)=N], 77,3 (NOCH₂), 65,3 (CH), 60,9 (CH₂—CH₂—N), 55,8 (OCH₃), 42,3 (Ph—CH₂), 54,6, 25,9 and 24,1 (pyperidine).

We claim:
1. Hydroximic acid derivatives of formula (I)

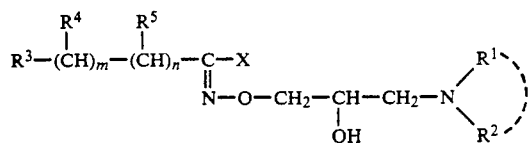

and the salts thereof wherein

X is selected from the group consisting of fluoro, chloro, bromo and iodo, $R^1$ and $R^2$ when taken together with the nitrogen to which these are attached form a heterocyclic ring selected from morpholinyl, piperazinyl or tetrahydroisoquinolinyl groups, $R^3$ is hydrogen, phenyl, naphthyl or optionally substituted with one or more halo or alkoxy, $R^4$ is hydrogen or phenyl, $R^5$ is hydrogen or phenyl, m is 0, 1 or 2 and n is 0, 1 or 4.

2. A pharmaceutical composition comprising at least one of the compounds of formula (I) as an active ingredient wherein said composition further comprises an acceptable carrier or diluent.

3. A method of treating diabetes angiopathy comprising administering compounds of formula (I) in an acceptable carrier.

* * * * *

UNITED STATES PATENT AND TRADEMARK OFFICE
CERTIFICATE OF CORRECTION

PATENT NO. : 5,328,906
DATED : July 12, 1994
INVENTOR(S) : Literati Nagy, et al.

It is certified that error appears in the above-indentified patent and that said Letters Patent is hereby corrected as shown below:

On the title page insert --[30] Foreign Application Priority Data
October 20, 1988  HU Hungary .... 5405/88--.

On the title page item [75], delete L. and substitute--Literati--.

Signed and Sealed this

Fourteenth Day of March, 1995

Attest:

BRUCE LEHMAN

*Attesting Officer*          *Commissioner of Patents and Trademarks*